United States Patent
Lim et al.

(10) Patent No.: US 9,878,961 B2
(45) Date of Patent: Jan. 30, 2018

(54) NICKEL-M-ALUMINA XEROGEL CATALYST, METHOD FOR PREPARING THE SAME, AND METHOD FOR PREPARING METHANE USING THE CATALYST

(75) Inventors: Hyo Jun Lim, Guri-si (KR); Chang Dae Byun, Seoul (KR); In Kyu Song, Suwon-si (KR); Dong Jun Koh, Seoul (KR); Sun Hwan Hwang, Seoul (KR); Jeong Gil Seo, Suwan-si (KR)

(73) Assignee: POSCO, Pohang-si (KR)

( * ) Notice: Subject to any disclaimer, the term of this patent is extended or adjusted under 35 U.S.C. 154(b) by 609 days.

(21) Appl. No.: 13/982,651

(22) PCT Filed: Dec. 28, 2011

(86) PCT No.: PCT/KR2011/010261
§ 371 (c)(1),
(2), (4) Date: Jul. 30, 2013

(87) PCT Pub. No.: WO2012/105756
PCT Pub. Date: Aug. 9, 2012

(65) Prior Publication Data
US 2013/0317127 A1 Nov. 28, 2013

(30) Foreign Application Priority Data
Jan. 31, 2011 (KR) .................... 10-2011-0009838

(51) Int. Cl.
*B01J 23/00* (2006.01)
*C07C 1/04* (2006.01)
(Continued)

(52) U.S. Cl.
CPC ............. *C07C 1/0435* (2013.01); *B01J 21/04* (2013.01); *B01J 23/74* (2013.01); *B01J 23/755* (2013.01);
(Continued)

(58) Field of Classification Search
CPC . B01J 21/04; B01J 23/74; B01J 23/755; B01J 23/78; B01J 23/83; B01J 23/883;
(Continued)

(56) References Cited

U.S. PATENT DOCUMENTS

| | | |
|---|---|---|
| 3,933,883 A | 1/1976 | Parthasarathy |
| 4,331,544 A | 5/1982 | Takaya et al. |
| 4,368,142 A | 1/1983 | Frohning et al. |
| 6,271,170 B1 | 8/2001 | Suh et al. |
| 6,355,219 B2 | 3/2002 | Suh et al. |

FOREIGN PATENT DOCUMENTS

CN 101884927 A 11/2010

OTHER PUBLICATIONS

Seo et al. "Hydrogen production by steam reformation of liquefied natural gas (LNG) over mesoporous nickel-alumina xerogel catalysts: Effect of nickel content" Jan. 8, 2008, Chemical Engineering Journal vol. 141, Issues 1-3, Jul. 15, 2008, pp. 298-304.*

(Continued)

*Primary Examiner* — Haytham Soliman
(74) *Attorney, Agent, or Firm* — The Webb Law Firm

(57) ABSTRACT

A nickel-M-alumina hybrid xerogel catalyst for preparing methane, wherein the metal M is at least one element selected from the group consisting of Fe, Co, Ni, Ce, La, Mo, Cs, Y, and Mg, a method for preparing the catalyst and a method for preparing methane using the catalyst are provided. The catalyst has strong resistance against a high-temperature sintering reaction and deposition of carbon species, and can effectively improve a conversion ratio of carbon monoxide and selectivity to methane.

2 Claims, 6 Drawing Sheets

(51) Int. Cl.
  *B01J 23/755* (2006.01)
  *B01J 23/83* (2006.01)
  *B01J 37/03* (2006.01)
  *B01J 21/04* (2006.01)
  *B01J 23/74* (2006.01)
  *B01J 23/78* (2006.01)
  *B01J 23/883* (2006.01)
  *B01J 35/10* (2006.01)

(52) U.S. Cl.
  CPC ............... *B01J 23/78* (2013.01); *B01J 23/83* (2013.01); *B01J 23/883* (2013.01); *B01J 35/1019* (2013.01); *B01J 35/1038* (2013.01); *B01J 35/1061* (2013.01); *B01J 37/036* (2013.01); *C07C 1/044* (2013.01); *C07C 2521/04* (2013.01); *C07C 2523/745* (2013.01); *C07C 2523/75* (2013.01); *C07C 2523/755* (2013.01); *C07C 2523/78* (2013.01); *C07C 2523/83* (2013.01); *C07C 2523/883* (2013.01)

(58) Field of Classification Search
  CPC ............... B01J 35/1019; B01J 35/1038; B01J 35/1061; B01J 37/036; C07C 1/044
  USPC ........................................................ 502/335
  See application file for complete search history.

(56) References Cited

OTHER PUBLICATIONS

Huang et al. "Fe Promoted Ni—Ce/Al2O3 in Auto-Thermal Reforming of Ethanol for Hydrogen Production" May 5, 2009, Catal Lett (2009) 130:432-439.*
Resini et al. "Yttria-stabilized zirconia (YSZ) supported Ni—Co alloys (precursor of SOFC anodes) as catalysts for the steam reforming of ethanol", International Journal of Hydrogen Energy, vol. 33, Issue 14, Jul. 2008, pp. 3728-3735, Jun. 13, 2008.*
Hwang et al. "Hydrogenation of carbon monoxide to methane over mesoporous nickel-M-alumina (M=Fe, Ni, Co, Ce, and La) xerogel catalysts" Journal of Industrial and Engineering Chemistry, vol. 18, Issue 1, Jan. 25, 2012, pp. 243-248, Nov. 4, 2011.*
Liu, Zhi Xin, "Preparation of Alumina Sol", Bulletin of the Chinese Ceramic Society, the fourth period, Aug. 28, 2004, p. 73.
Vannice;"The Catalytic Syntheses of Hydrocarbons from H2CO Mixtures Over the Group VIII Metals"; J. Catal.; vol. 37; 1975 ; p. 449.
Ozdogan et al.; "Carbon and Carbon Monoxide Hydrogenation on Nickel: Support Effects"; J. Catal.; vol. 83; 1983; p. 257.
Hwang et al.; "Methane Production from Carbon Monoxide and Hydrogen Over Nickel-Alumina Xerogel Catalyst: Effect of Nickel Content" ; J. Indus./Eng. Chem.; vol. 17, 2011; pp. 154-157.

* cited by examiner

NICKEL-M-ALUMINA XEROGEL CATALYST, METHOD FOR PREPARING THE SAME, AND METHOD FOR PREPARING METHANE USING THE CATALYST

CROSS-REFERENCE TO RELATED APPLICATIONS

This application is the United States national phase under 35 U.S.C. § 371 of International Application No. PCT/KR2011/010261 filed Dec. 28, 2011, entitled "Nickel-M-Alumina Xerogel Catalyst, Method for Preparing the Same, and Method for Preparing Methane Using the Catalyst" and claims priority under 35 U.S.C. § 119(a)-(d) to Korean Application No. 10-2011-0009838, filed Jan. 31, 2011, in the Korea Intellectal Property Office, the disclosures of which are hereby incorporated by reference in their entirety.

CROSS-REFERENCE TO RELATED APPLICATION

This application claims priority to and the benefit of Korean Patent Application No. 2011-0009838, filed Jan. 31, 2011, the disclosure of which is incorporated herein by reference in its entirety.

BACKGROUND

1. Field of the Invention

The present invention relates to a nickel-M-alumina xerogel catalyst, a method for preparing the same, and a method for preparing methane using the catalyst.

2. Discussion of Related Art

In modern society, ensuring energy sources is an essential factor in terms of economic and industrial development. The importance of energy sources has increased in accordance with the rapid increase in energy consumption and the appearance of limitations on recoverable oil reserves. Also, the atmospheric pollution has become serious with a sudden increase in consumption of fossil energy. In developed countries such as several European countries and Japan, development of renewable energy technology has accelerated. Among fossil fuels, natural gas is a gaseous hydrocarbon naturally produced underground like petroleum. Natural gas is a fuel that contains methane ($CH_4$) as a main component, and is clean enough to prevent environmental pollution, stable and convenient. Accordingly, natural gas has come into the spotlight as an alternative energy of a solid fuel such as petroleum, coal, etc. For this reason, natural gas has been widely used in various fields such as homes, commerce, transportation, and industries, and forms the basis of global energy industries together with petroleum and coal as an energy source which amounts to approximately ¼ of global energy consumption. In spite of an increase in the demand for natural gas, however, the supplies and prices are unstable due to limitations on recoverable natural gas reserves on the Earth and fluctuation of oil prices. To solve these problems, countries having low natural gas reserves have conducted much research on synthetic natural gas.

The term "synthetic natural gas" or "substitute natural gas" (SNG) refers to artificially produced natural gas. In recent years, there has been much research conducted to prepare methane as a main component of natural gas from coal, biomass, or petroleum coke. Especially, a method of preparing synthetic natural gas from coal is expected to be a main energy source in the future in terms of stabilization of high prices of conventional natural gas using rich gas reserves and diversification of fuels.

Methods of preparing synthetic natural gas from coal include a method of obtaining methane by subjecting a synthetic gas obtained through coal gasification to a methane synthetic reaction using a catalyst (gasification method), a method of obtaining synthetic natural gas by allowing coal to directly react with hydrogen (hydrogasification method), and a method of obtaining synthetic natural gas by allowing coal to react with steam at a low temperature using a catalyst (catalytic gasification method).

The catalyst obtained according to the present invention is a catalyst used to synthesize methane from a synthetic gas obtained from coal through a gasification method. To perform a methanation reaction on the synthetic gas, research on various metal catalysts such as Ni, Re, Ru, Rh, Pt, Fe and Co has been conducted [M. V. Vannice, J. Catal., 37 vol., page 449 (1975)]. Among these, Ru and Co catalysts were reported to show the highest activities, but have a disadvantage in that their price competitiveness is very low. Ni has been commercially used due to price competitiveness and high reactivity, but has problems in that its reaction activity is lower than those of Ru and Co, and it may be deactivated by deposition and particle sintering reactions of carbon species as the reactions are in progress.

Also, the reactivity of a catalyst for a methanation reaction is highly affected by the kind of a carrier. So far, various kinds of supports such as $Al_2O_3$, $SiO_2$, $TiO_2$, $La_2O_3$ and $CeO_2$ have been reported [S. Z. Ozdogan, P. D. Gochis, J. L. Falconer, J. Catal., 83 vol., page 257 (1983)]. Among these, $Al_2O_3$ has the highest thermal stability, and may enhance a yield of methane due to its proper interaction with an active metal.

SUMMARY OF THE INVENTION

The present invention is directed to providing a nickel-M-alumina xerogel catalyst and a method for preparing the same. Also, the present invention is directed to providing a method for preparing methane using the catalyst.

One aspect of the present invention provides a nickel-M-alumina xerogel catalyst. Here, the metal M is at least one element selected from the group consisting of Fe, Co, Ni, Ce, La, Mo, Cs, Y, and Mg.

Another aspect of the present invention provides a method for preparing a nickel-M-alumina hybrid xerogel catalyst. Here, the method includes forming an aluminum precursor sol, forming a nickel-M-alumina sol by mixing the prepared aluminum precursor sol, a nickel precursor and an M precursor, forming a nickel-M-alumina gel by mixing the nickel-M-alumina sol with water, and aging, drying and plasticizing the nickel-M-alumina gel.

Still another aspect of the present invention provides a method for preparing methane using the catalyst. Here, the method includes performing a hydrogenation reaction by passing carbon monoxide, hydrogen and nitrogen through a nickel-M-alumina xerogel catalyst.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DESCRIPTION OF THE INVENTION

Figure 1:
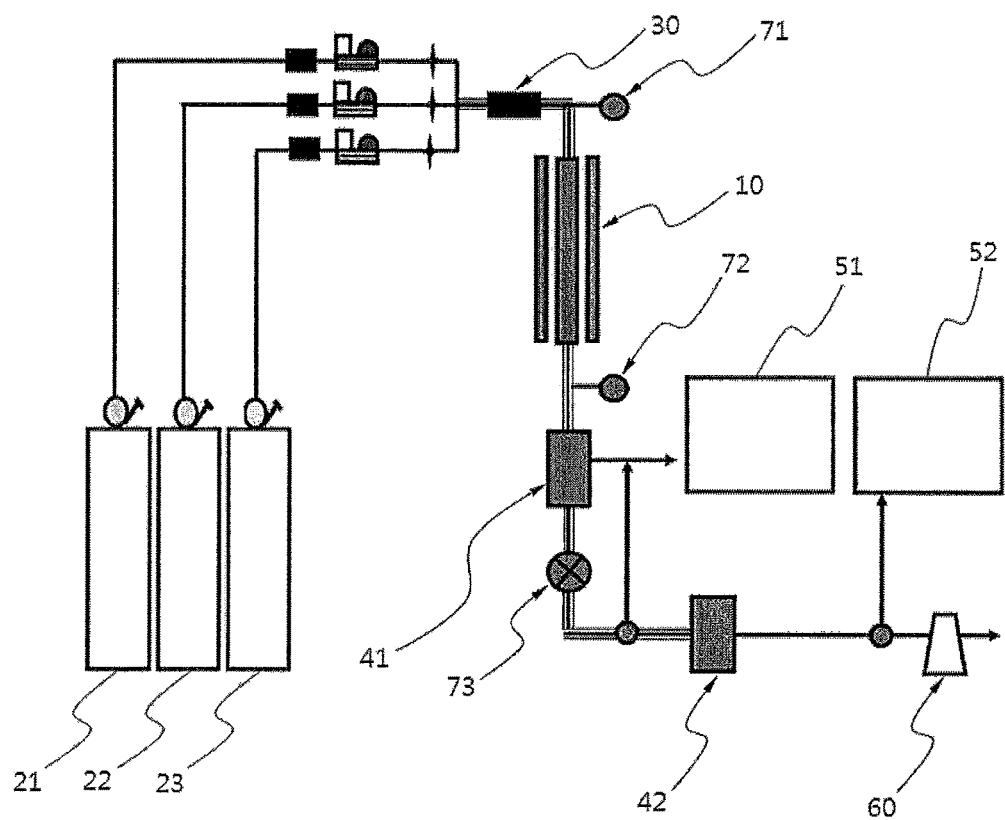
FIG. 1 is a schematic view of a continuous flow reactor according to one exemplary embodiment of the present invention.

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

The present invention is directed to providing a nickel-M-alumina hybrid xerogel catalyst for preparing methane. Here, the metal M is at least one element selected from the group consisting of Fe, Co, Ni, Ce, La, Mo, Cs, Y, and Mg. The nickel-M-alumina catalyst may be effectively used to prepare methane through a hydrogenation reaction of carbon monoxide. According to the present invention, a methanation reaction or a hydrogenation reaction of carbon monoxide means a process for preparing methane through a reaction between carbon monoxide and hydrogen.

The nickel-M-alumina xerogel catalyst according to the present invention may include nickel at 1 to 50 parts by weight, and M (i.e., a metal) at 1 to 20 parts by weight, based on a total of 100 parts by weight of the catalyst. More particularly, the catalyst may include nickel at 15 to 40 parts by weight, and M (i.e., a metal) at 5 to 15 parts by weight, based on a total of 100 parts by weight of the catalyst. For example, a content of the nickel may be 30 parts by weight, and a content of the metal M may be 10 parts by weight. When the content of the nickel is less than this content range, reactivity may be degraded. When the content of the metal M is less than this content range, the catalyst may be inactivated by deposition and particle sintering reactions of carbon species. When the content of the nickel or metal M exceeds this content range, contents of the other components may be excessively reduced.

Pores formed in the catalyst of the present invention may have an average diameter of 1 to 5 nm, especially 2 to 4 nm. The mesoporous nickel-M-alumina catalyst may inhibit formation of carbon species having a suitable size to facilitate deposition of carbon (C) on a surface of the catalyst due to the mesopores uniformly formed by a one-step sol-gel method and highly dispersed metal particles. Also, the mesoporous nickel-M-alumina catalyst has excellent resistance against carbon deposition, and characteristically shows almost no catalyst inactivation caused by sintering of the metal particles even when the catalyst is driven for a long period of time. In particular, when the metal M is added, the nickel-alumina catalyst may have new properties due to interaction between the nickel and the metal M in addition to the characteristics. For such properties, for example, the nickel-M-alumina catalyst has low CO dissociation energy, and shows higher reactivity and selectivity than a conventional methanation catalyst. The metal M may be at least one selected from the group consisting of Fe, Co, Ni, Ce, La, Mo, Cs, Y, and Mg. For example, the metal M may be at least one of Fe, Co, Ni, Ce and La, at least one of Co, Ni, Ce and La, at least one of Co, Ce and La, or Fe.

According to one exemplary embodiment, the catalyst according to the present invention may have a specific surface area of 100 to 350 m$^2$/g, or 120 to 300 m$^2$/g. In this specific surface area range, selectivity to methane may be enhanced, and deposition of carbon (C) formed on a surface of the catalyst may be reduced.

In the present invention, the term "nickel-M-alumina" refers to a state in which nickel, a metal M and alumina are hybridized, and, for example, has a structure in which nickel and a metal M are uniformly dispersed in spinel-type alumina showing moderate crystallinity. Also, in the present invention, a xerogel is a dried gel, and has a porous structure in which a solvent is removed from gaps between gel networks, which are then filled with air.

When the nickel-M-alumina xerogel catalyst according to the present invention is subjected to a hydrogenation reaction, a conversion ratio of carbon monoxide may be in a range of 80 to 100%, selectivity to methane in a hydrocarbon may be in a range of 60 to 90%, and selectivity of carbon dioxide may be in a range of 5 to 10%. From this fact, it can be seen that the nickel-M-alumina xerogel catalyst according to the present invention is a catalyst suitable for preparing methane through a hydrogenation reaction of carbon monoxide.

Also, the present invention is directed to providing a method for preparing the above-described nickel-M-alumina xerogel catalyst.

According to one exemplary embodiment, the preparation method may include:

(i) forming an aluminum precursor sol;

(ii) forming a nickel-M-alumina sol by mixing the prepared aluminum precursor sol, a nickel precursor and an M precursor;

(iii) forming a nickel-M-alumina gel by mixing the nickel-M-alumina sol with water, and (iv) aging, drying and plasticizing the nickel-M-alumina gel. Here, the metal M may be at least one element selected from the group consisting of Fe, Co, Ni, Ce, La, Mo, Cs, Y, and Mg.

Hereinafter, each operation of the method for preparing a nickel-M-alumina catalyst according to the present invention will be described in further detail.

Operation (i) is an operation of forming an aluminum precursor sol. More particularly, operation (i) may include dissolving an aluminum precursor in an alcohol solvent heated at a temperature of 50 to 80° C., and obtaining a transparent sol by mixing the solution in which the aluminum precursor is dissolved with a small amount of water diluted with the alcohol solvent, and an acid and partially hydrating the resulting mixture.

The alcohol solvent may be used without regard to the type, but ethanol is preferably used. For example, an alumina precursor may be added, and dissolved in an alcohol solvent heated at 50 to 80° C. while stirring. The aluminum precursor added with respect to the alcohol solvent may be mixed at a content of 10 to 30 parts by weight, based on 100 parts by weight of the alcohol. Also, the alcohol solvent may be maintained at a temperature of 50° C. to 80° C. This is because it is difficult to synthesize a sol at a temperature of 50° C. or less, and the alcohol solvent is evaporated at a temperature of 80° C. or more.

The aluminum precursor may be mixed at a content of 10 to 30 parts by weight, based on 100 parts by weight of the alcohol. When the content of the aluminum precursor is less than 10 parts by weight, a gel may be formed due to a relative increase in the amount of the alcohol, but a gel formation time is long, and it is difficult to completely form a gel. On the other hand, when the content of the aluminum precursor exceeds 30 parts by weight, an amount of the alcohol present between aluminum components during formation of a gel may be reduced due to a relative increase in the amount of aluminum, which makes it difficult to facilitate formation of pores.

Meanwhile, the kind of the aluminum precursor is not particularly limited. For example, the aluminum precursor may be at least one selected from the group consisting of aluminum nitrate nonahydrate, aluminum fluoride trihydrate, aluminum phosphate hydrate, and aluminum chloride hexahydrate.

Operation (ii) is an operation of forming a nickel-M-alumina sol by mixing the prepared aluminum precursor sol with a nickel precursor and an M precursor. Operation (ii) may include cooling the prepared aluminum precursor sol to 40 to 60° C., and forming a nickel-M-alumina sol by mixing the cooled aluminum precursor sol with the nickel precursor and the M precursor.

A content of the nickel precursor may be in a range of 1 to 50 parts by weight, particularly 15 to 40 parts by weight. Also, a content of the M precursor may be in a range of 1 to 20 parts by weight, particularly 5 to 15 parts by weight. This content range represents a content based on a total of 100 parts by weight of the catalyst with respect to the metal components of the catalyst.

The nickel precursor and the M precursor may be precursors in the form of a metal acetate hydrate or a metal chloride hydrate. The kind of the metal M may be at least one metal selected from the group consisting of Fe, Co, Ni, Ce, La, Mo, Cs, Y, and Mg.

Operation (iii) is an operation of forming a nickel-M-alumina gel by mixing the nickel-M-alumina sol with water and an alcohol solvent. More particularly, the nickel-M-alumina sol is cooled at room temperature, and a small amount of water in which the alcohol solvent is diluted is then added to form a nickel-M-alumina gel.

In operation (iii), a time required to convert the nickel-M-alumina sol into the nickel-M-alumina gel may be in a range of several hours to several tens of hours, and is affected by the nickel precursor and the M metal precursor. The added metal is bound to braches of the aluminum precursor to form a gel. Here, the M metal occupies different positions on the periodic table of elements, and thus has different atomic radii and electrical potentials. This affects a condensation rate at which the nickel-M-alumina sol is converted into a gel. As a result, a time required to form a gel may be in a range of several hours to several tens of hours, depending on the kind of the added M metal.

A mixing ratio of the alcohol solvent and water to form a gel is not particularly limited. For example, water may be mixed at a content of 15 to 100 parts by weight, based on 100 parts by weight of the alcohol. When the water is added at a content of less than 15 parts by weight, a gel may not be formed. On the other hand, when the content of the water exceeds 100 parts by weight, an opaque gel may be formed while forming fine particles. Such a gel serves to prevent the finally produced nickel-M-alumina from exhibiting uniform physical properties.

Operation (iv) is an operation of aging, drying and plasticizing the nickel-M-alumina gel. More particularly, operation (iv) may include aging the nickel-M-alumina gel for 3 to 10 days, drying the nickel-M-alumina gel at 60 to 80° C., and plasticizing the nickel-M-alumina gel at 600 to 900° C. for 3 to 10 hours.

The aging of the gel may be performed at room temperature for 3 to 10 days. In the aging operation, hydration and condensation reactions which are not completely performed in the previous operation are completed. In this case, the aging operation affects the physical characteristics of the catalyst. When an aging time is excessively long or short, a structure of the catalyst is not completely formed, thereby forming a gel having a surface area, pore volume and pore size smaller than desired levels.

The surface area, pore volume and pore size of the aged gel may vary according to a drying temperature. For example, the drying of the aged gel may be performed at 60 to 80° C. in a state in which a steam pressure is controlled by closing an opening of a container with a holed aluminum foil. 10 to 20 holes may be formed in the aluminum foil to dry a gel at a controlled rate. When the number of the holes is less than 10, a drying time is increased to cause shrinkage in a structure of the catalyst, and a time required to dry a gel is also increased. On the other hand, when the number of the holes exceeds 20, the gel cracks and collapses due to an increase in drying rate, which makes it difficult to form a gel having a desired surface area, pore volume and pore size. Also, when a drying temperature is less than 60° C., the gel is exposed to heat for a long period of time. As a result, shrinkage in structure of the catalyst takes place during drying of the solvent, which makes it difficult to form a gel having a surface area, pore volume and pore size suitable for a reaction. On the other hand, when the drying temperature exceeds 80° C., the gel undergoing the aging operation turns into a sol again due to a high temperature, and a network structure formed during gel formation may be collapsed.

In the plasticizing operation, when a heat treatment temperature is less than 600° C., it is difficult to ensure thermal stability of the catalyst with respect to heat generated during a methanation reaction of carbon monoxide. On the other hand, when the heat treatment temperature exceeds 900° C., a structure and porosity of the catalyst may collapse due to sintering of nickel particles, and desirable catalytic activities may not be achieved.

The present invention is also directed to providing a method for preparing methane using the above-described nickel-M-alumina catalyst. The method may provide a method for preparing methane from carbon monoxide through a hydrogenation reaction.

According to one exemplary embodiment, the method for preparing methane may include performing a hydrogenation reaction by passing carbon monoxide, hydrogen and nitrogen through the nickel-M-alumina xerogel catalyst. Here, the metal M may be at least one element selected from the group consisting of Fe, Co, Ni, Ce, La, Mo, Cs, Y, and Mg. For example, the metal M may be at least one of Fe, Co, Ni, Ce and La, at least one of Co, Ni, Ce and La, at least one of Co, Ce and La, or Fe.

More particularly, the method for preparing methane may include pretreating the nickel-M-alumina xerogel catalyst with hydrogen and nitrogen gas (operation A), and passing carbon monoxide, hydrogen and nitrogen through the pretreated nickel-M-alumina xerogel catalyst (operation B).

The pretreatment of operation A may be performed for 3 to 10 hours by allowing nitrogen and hydrogen to flow at rates of 30 ml/min and 3 to 15 ml/min, respectively, at 650 to 850° C. in a continuous flow reactor for a methanation reaction.

The nickel and M metal in the nickel-M-alumina catalyst prepared through the plasticizing operation are present in an oxidized state. Since the nickel and M metal in the oxidized state show no reactivity to a hydrogenation reaction of carbon monoxide, the nickel and M metal should be reduced with hydrogen to be activated. The metals in the oxidized state are bound to each other while undergoing a reduction reaction, thereby forming particles. In this case, reduction conditions are set using a method of flowing hydrogen only and a method of flowing hydrogen with nitrogen. Among these, in the method of flowing hydrogen with nitrogen, the oxidizing species such as nickel and an M metal present on an alumina surface are reduced to form fine metal particles. According to the present invention, a method of reducing the oxidizing species by allowing nitrogen and hydrogen to flow at rates of 30 ml/min and 3 to 15 ml/min, respectively, has an effect of converting the oxidizing species such as nickel and an M metal present on a surface of the nickel-M-alumina catalyst into an activated metal having a suitable particle size to perform a methanation reaction.

A pretreatment temperature may be in a range of 650 to 850° C. Within this pretreatment temperature range, all the oxidizing species such as metals present on a surface of the catalyst may be activated. When the pretreatment temperature is less than 650° C., some of the metal oxidizing species are not reduced and remain oxidized. As a result, the metals in an oxidized state affect reactivity since they do not take part in a methanation reaction. On the other hand, when the pretreatment temperature is greater than 850° C., a sintering reaction of metals and reduction of the metal oxidizing species are performed, which leads to a decrease in active sites.

A level of reduction of the nickel and M metal is determined according to a pretreatment time. To reduce the oxidizing species such as nickel and an M metal present on a surface of the catalyst, a reduction operation should be performed for at least a predetermined time. For example, the pretreatment time may be in a range of 3 to 10 hours. When the reduction operation is performed for at least a predetermined time, all the metals in an oxidized state present on the surface of the catalyst are reduced. Therefore, it is unnecessary to perform the reduction operation for a longer period of time.

Operation B is an operation of performing a hydrogenation reaction by passing carbon monoxide, hydrogen and nitrogen through the pretreated nickel-M-alumina xerogel catalyst.

In the hydrogenation reaction, a synthetic gas including carbon monoxide and hydrogen, and nitrogen may be supplied at a space velocity of 100 to 30,000 ml/h·g-catalyst, and, more particularly, a space velocity of 1,000 to 10,000 ml/h·g-catalyst. In the hydrogenation reaction, a pressure may be in a range of 0.001 to 50 bars, particularly 0.01 to 20 bars, and a reaction temperature may be in a range of 200 to 400° C., particularly 230 to 340° C.

When the hydrogenation reaction is performed, a volume ratio between carbon monoxide and hydrogen may be in a range of 1:1 to 1:5, particularly 1:2 to 1:4, so as to maximize a conversion rate of carbon monoxide and hydrogen and minimize carbon deposition. To ensure sufficient methane production, for example, a volume ratio between carbon monoxide and hydrogen may be adjusted to 1:3. When the volume ratio of carbon monoxide is excessively low, production of carbon monoxide may be reduced. On the other hand, when the volume ratio of carbon monoxide is excessively high, carbon deposition is increased during a reaction between carbon monoxide and hydrogen, which leads to a sudden decrease in activity of the catalyst.

Also, a volume ratio between carbon monoxide and nitrogen may be in a range of 1:1 to 1:4. Since a methanation reaction is an exothermic reaction in which a large amount of heat is generated, heat of reaction is not effectively dispersed when the conversion rate exceeds a predetermined conversion rate. To effectively disperse the heat of reaction, a reaction product should be diluted by adding an inert gas together with a reactive gas. When the volume ratio of nitrogen is less than this volume ratio range, it is difficult to effectively disperse the heat of reaction. On the other hand, when the volume ratio of nitrogen exceeds this volume ratio range, methane selectivity may be degraded.

When the space velocity increases in a hydrogenation reaction of carbon monoxide, methane selectivity may be degraded, and production of hydrocarbon and carbon dioxide increases to an undesirable level. On the other hand, when the space velocity decreases, methane selectivity may be improved. Since a maximum value exists for the methane selectivity, the space velocities of nitrogen and a synthetic gas including carbon monoxide and hydrogen may be in a range of 100 to 30,000 ml/h·g-catalyst, particularly 1,000 to 10,000 ml/h·g-catalyst.

As the reaction pressure increases in the hydrogenation reaction of carbon monoxide, a conversion rate and methane selectivity tend to increase. However, when the reaction pressure is greater than 50 bars, the conversion rate reaches the maximum value. As a result, a further increase in pressure may lead to efficiency reduction.

Also, the catalyst for a hydrogenation reaction of carbon monoxide should be exposed to a temperature greater than a predetermined temperature so as to show activity. Since the catalyst is not reactive at a temperature of less than 200° C., a hydrogenation reaction of carbon monoxide does not take place. On the other hand, since the conversion rate of carbon monoxide and methane selectivity reach the maximum values at a temperature of greater than 400° C., a hydrogenation reaction of carbon monoxide may be performed at a reaction temperature of 200 to 400° C., particularly 230 to 340° C.

When a hydrogenation reaction is performed using the nickel-M-alumina xerogel catalyst according to the present invention, a conversion rate of carbon monoxide may be in a range of 80 to 100%, selectivity to methane in the hydrocarbon may be in a range of 60 to 90%, and selectivity to carbon dioxide may be in a range of 5 to 10%. As a result, it can be seen that the nickel-M-alumina xerogel catalyst is suitable for preparing methane using a hydrogenation reaction of carbon monoxide.

FIG. 1 is a schematic view of a continuous flow reactor according to one exemplary embodiment of the present invention. Referring to FIG. 1, hydrogen, nitrogen and carbon monoxide are supplied from storage units 21, 22 and 23 to a reactor 10 through a mixing chamber 30. In this case, a supply flow rate may be controlled by means of a pressure indicator 71. A reactor 10 is filled with a nickel-M-alumina xerogel catalyst, and a hydrogenation reaction is initiated while bringing the supplied hydrogen, nitrogen and carbon monoxide into contact with the catalyst in the reactor 10. Methane gas produced by means of a hydrogenation reaction is passed through a hot trap 41 and a cold trap 42, and stored through a gas outlet 60. A hot trap 41 is connected with a flame ionization detector 51, and a stream between the hot trap 41 and a cold trap 42 is also connected with the flame ionization detector 51. A stream passed through the cold trap 42 is connected with a thermal conductivity detector 52. A pressure sensor 72 may be provided between the reactor 10 and the hot trap 41, and a pressure regulator 73 may be provided between the hot trap 41 and the cold trap 42.

Hereinafter, the present invention will be described in further detail with reference to the following Preparation Examples and Examples. However, it should be understood that the following Preparation Examples and Examples are given by way of illustration of the present invention only, and are not intended to limit the scope of the present invention.

Preparation Example 1: Preparation of Nickel-Fe-Alumina Xerogel Catalyst

An ethanol solvent was heated at 80° C. while stirring. 7 g of an aluminum precursor, aluminum sec-butoxide (Al[OCH(CH$_3$)C$_2$H$_5$]$_3$, Aldrich), was dissolved in the heated ethanol solvent. A mixture solution of ethanol (40 ml), nitric acid (0.1 ml) and water (0.3 ml) was slowly added to the resulting solution while maintaining the solution at a temperature of 80° C. Simultaneously, a partial hydration reaction was performed to obtain a transparent alumina sol.

The prepared alumina sol was cooled to 50° C., and nickel acetate tetrahydrate (C$_4$H$_6$NiO$_4$.H$_2$O, Aldrich) and iron acetate (Fe(CO$_2$CH$_3$)$_2$, Aldrich), both of which were dispersed in 10 ml of ethanol, were added thereto to obtain a nickel-Fe-alumina sol. An amount of the nickel precursor was added so that a content of nickel amounted to 30 parts by weight, based on a total of 100 parts by weight of the prepared catalyst, and an amount of the Fe metal precursor was added so that an Fe content amounted to 10 parts by weight, based on a total of 100 parts by weight of the prepared catalyst.

The prepared nickel-Fe-alumina sol was cooled at room temperature, and a mixture solution of ethanol (5 ml) and water (0.6 ml) was slowly injected to obtain a nickel-M-alumina gel, which was then aged at room temperature for 7 days.

The aged gel was slowly dried for 72 hours in an oven at a constant temperature of 70° C. until ethanol was completely removed. As a result, a nickel-Fe-alumina xerogel was obtained. The finally prepared nickel-Fe-alumina xerogel was heat-treated at 700° C. for 5 hours in an electric oven to prepare a xerogel nickel-Fe-alumina catalyst.

The prepared catalyst was named 30Ni10Fe. Here, the numerals 30 and 10 written before Ni and Fe refer to the weights (units: parts by weight) of nickel and iron, based on a total of parts by weight of the catalyst.

Preparation Example 2: Preparation of Nickel-M-Alumina Xerogel Catalyst Including Different M Metals Mesoporous nickel-M-alumina xerogel catalysts were prepared according to the preparation method described in Preparation Example 1, except that different kinds of M metals were used instead of the nickel.

More particularly, the nickel-M-alumina xerogel catalysts (M=Ni, Co, Ce, and La) were prepared, respectively, using nickel acetate tetrahydrate (C$_4$H$_6$NiO$_4$.H$_2$O, Aldrich), cobalt acetate tetrahydrate ((CH$_3$CO$_2$)$_2$Co.H$_2$O, Aldrich), cerium acetate hydrate ((CH$_3$CO$_2$)$_3$Ce.xH$_2$O, Aldrich), and lanthanum acetate hydrate ((CH$_3$CO$_2$)$_3$La.xH$_2$O, Aldrich) as the M metal precursors.

The prepared catalysts were named 30Ni10Ni, 30Ni10Co, 30Ni10Ce and 30Ni10La, respectively. Here, the numerals 30 and 10 written before Ni and M refer to the weights (units: parts by weight) of nickel and the M metal, based on a total of 100 parts by weight of the catalyst.

Experimental Example 1: ICP-AES Analysis and Physical Characteristics of Nickel-M-Alumina Xerogel Catalyst To determine basic characteristics of the prepared nickel-M-alumina catalysts, ICP-AES analyses were performed on the catalysts, and specific surface areas, pore volumes and average pore sizes of the catalysts were measured. The results are listed in Table 1.

TABLE 1

| Catalyst | Ni content (parts by weight) | M content (parts by weight) | Specific surface area (m$^2$/g) | Pore volume (cm$^3$/g) | Average pore size (nm) |
|---|---|---|---|---|---|
| 30Ni10Fe | 31.2 | 9.8 | 164 | 0.21 | 3.4 |
| 30Ni10Co | 30.8 | 10.6 | 138 | 0.17 | 3.4 |
| 30Ni10Ni | 30.0 | 9.8 | 296 | 0.28 | 2.7 |
| 30Ni10Ce | 32.0 | 8.7 | 223 | 0.21 | 2.7 |
| 30Ni10La | 31.5 | 8.9 | 207 | 0.19 | 2.7 |

From the ICP-AES analysis results as listed in Table 1, it could be seen that a nickel-M-alumina catalyst, which included nickel at 30 parts by weight and an M metal at 10 parts by weight based on a total of 100 parts by weight of the catalyst, was prepared as a title catalyst.

As listed in Table 1, it could be seen that the 30Ni10Fe, 30Ni10Co, 30Ni10Ni, 30Ni10Ce and 30Ni10La catalysts prepared in the present invention were nickel-M-alumina xerogels having mesopores in the backbone structure. From the results listed in Table 1, it could be seen that the 30Ni10Ni catalyst including only a single metal had a higher surface area and pore volume than the 30Ni10M catalyst including a single metal in addition to different kinds of M metals such as Fe, Co, Ce, and La.

Figure 2:
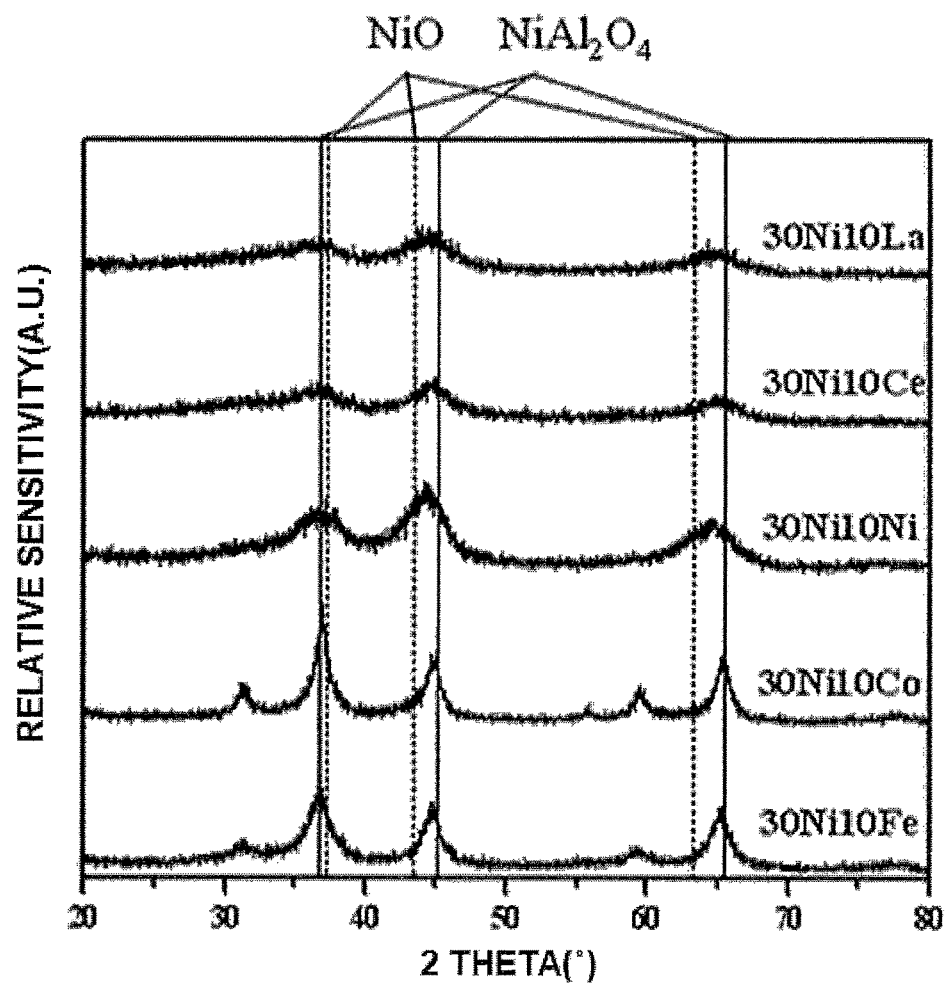
FIG. 2 is a graph illustrating the X-ray diffraction analysis results of nickel-M-alumina xerogel catalysts prepared in Preparation Examples 1 and 2 before reduction of the nickel-M-alumina xerogel catalysts.
Figure 3:
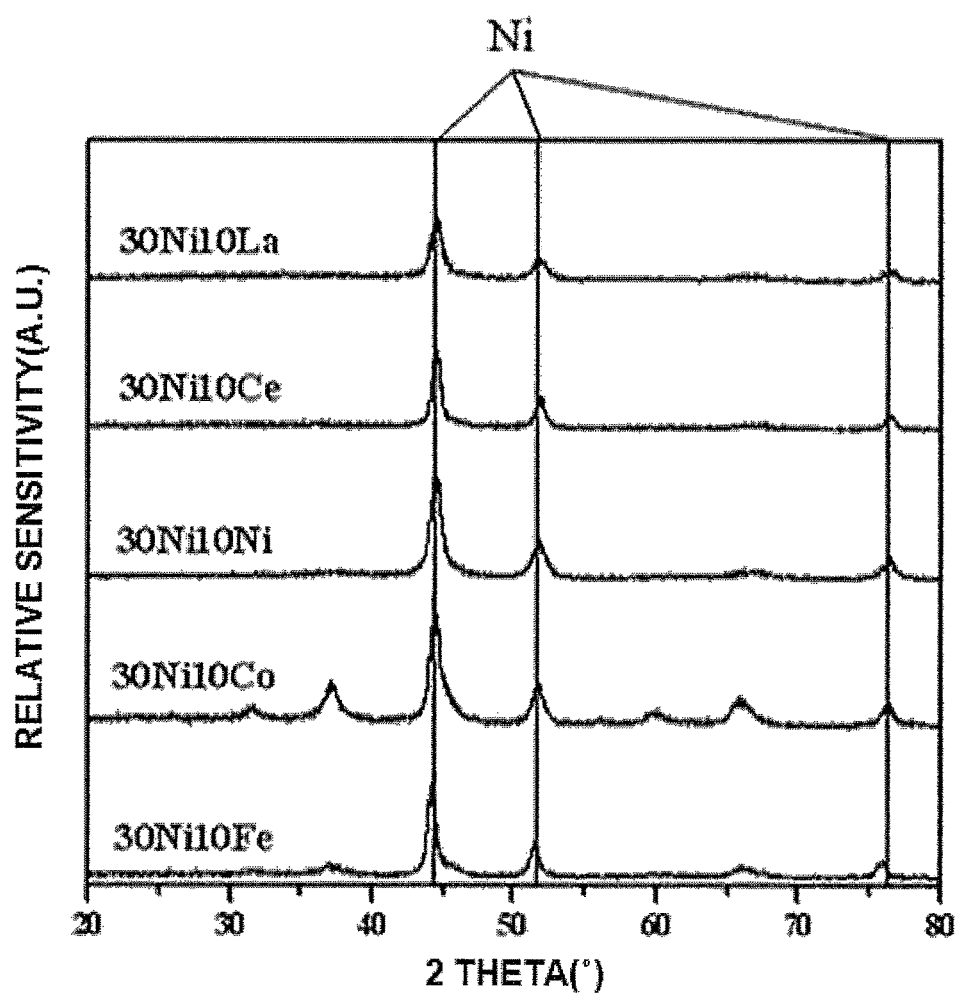
FIG. 3 is a graph illustrating the X-ray diffraction analysis results of the nickel-M-alumina xerogel catalysts prepared in Preparation Examples 1 and 2 after reduction of the nickel-M-alumina xerogel catalysts.

Experimental Example 2: X-Ray Diffraction Analysis Results of Nickel-M-Alumina Xerogel Catalyst FIGS. 2 and 3 are graphs illustrating the X-ray diffraction analysis results of nickel-M-alumina xerogel catalysts prepared in Preparation Examples 1 and 2 before/after reduction of the nickel-M-alumina xerogel catalysts. Referring to FIG. 2 showing the X-ray diffraction analysis results before reduction of the respective catalysts, it could be seen that characteristic peaks of the nickel and M metal overlapped and were not exactly separated from each other, but grew into an aluminate phase. FIG. 3 shows the X-ray diffraction analysis results after reduction of the respective catalysts at 700° C. From these analysis results, it could be seen that all the nickel oxidizing species and the M metal oxidizing species were reduced, and were bound to each other during a reduction reaction to form a new phase.

Figure 4:
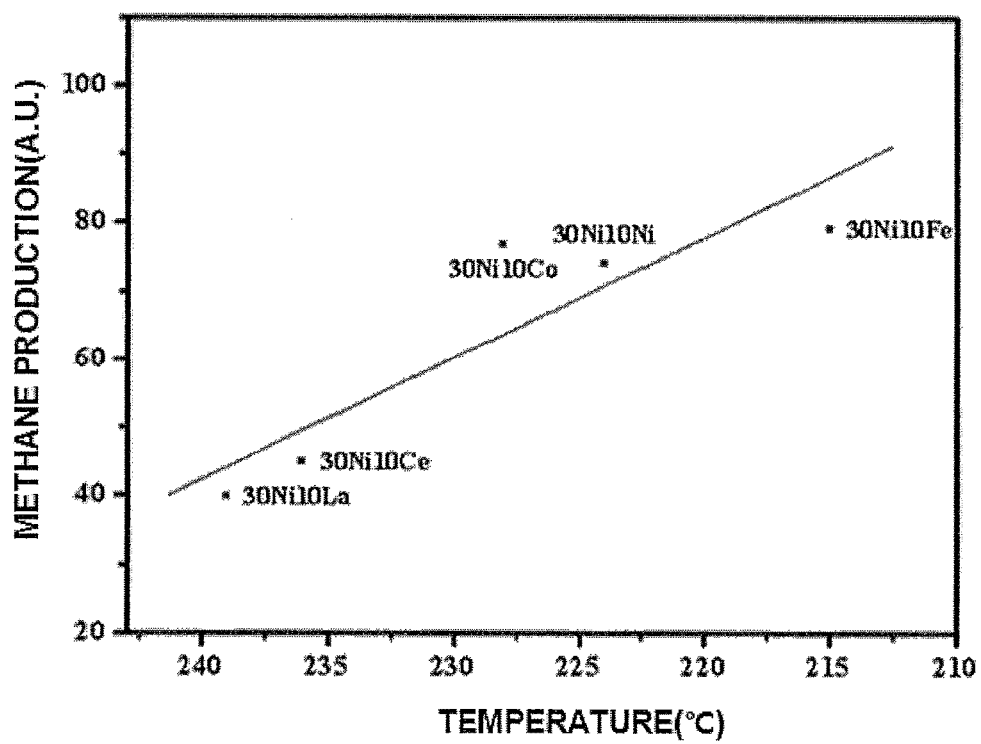
FIG. 4 is a graph illustrating the temperature-programmed surface reaction results of the nickel-M-alumina xerogel catalysts prepared in Preparation Examples 1 and 2.

Experimental Example 3: Temperature-Programmed Surface Reaction Analysis of Nickel-M-Alumina Xerogel Catalyst To determine a difference in characteristics of the nickel-M-alumina xerogel catalysts prepared in Preparation Examples 1 and 2, a temperature-programmed surface reaction (TPSR) test was performed. The results are shown in FIG. 4. To perform a temperature-programmed surface reaction test, a U-shaped quartz tube was filled with 0.1 g of each of the nickel-M-alumina xerogel catalysts prepared in Preparation Examples 1 and 2. Thereafter, a reduction reaction was performed at 700° C. for 5 hours while allowing a mixed gas including helium (30 ml/min) and hydrogen (3 ml/min) to flow through the quartz tube, and the catalysts in the quartz tube were cooled at room temperature. Then, carbon monoxide was adsorbed onto a surface of an activated metal so that the surface of the activated metal was saturated with the carbon monoxide while allowing a mixed gas including carbon monoxide (3 ml/min) and helium (5 ml/min) to flow for an hour through the quartz tube. After adsorption of the carbon monoxide, helium (30 ml/min) was allowed to flow for 30 minutes through the activated metal so as to remove the carbon monoxide physically adsorbed on a surface of the activated metal.

A temperature-programmed surface reaction on the nickel-M-alumina catalyst layer undergoing the above-described pretreatment process was performed under an atmosphere of mixed gas of hydrogen (1 mL/min) and helium (9 ml/min) while warming the nickel-M-alumina catalyst layer at a rate of 10° C./min.

A discharged gas passed through the catalyst was analyzed using a mass spectroscope to measure an amount of methane produced during a heating process. From this fact, it could be seen that the characteristics of each catalyst in a hydrogenation reaction of carbon monoxide were determined. The results are shown in FIG. 4.

Referring to FIG. 4, it could be seen that each catalyst had a peak derived from methane produced at a certain temperature. In the methanation reaction, dissociation of carbon monoxide into intermediate carbon (C*) and oxygen (O) was considered to be an important process determining the reactivity. In the temperature-programmed surface reaction results, generation of a peak at a certain temperature means that a reaction in which carbon monoxide adsorbed onto a surface of a catalyst was dissociated into intermediate carbon and oxygen and the intermediate carbon reacted with hydrogen to form methane was activated. Therefore, it could be seen that the catalyst by which a peak derived from methane was produced at a low temperature was desirable for a methanation reaction since it had a low dissociation energy of carbon monoxide.

A decrease in characteristic peaks was produced in the order of the 30Ni10Fe, 30Ni10Ni, 30Ni10Co, 30Ni10Ce and 30Ni10La catalysts.

Experimental Example 4: CHNS Analysis Results of Nickel-M-Alumina Xerogel Catalyst Recovered after Reaction After methanation reaction of the nickel-M-alumina xerogel catalysts prepared in Preparation Example 1 and 2, carbon deposition amounts of the catalysts were measured using CHNS analysis. The results are listed in Table 2.

TABLE 2

| Catalyst | Carbon deposition amount (%) |
| --- | --- |
| 30Ni10Fe | 0.7 |
| 30Ni10Co | 2.6 |
| 30Ni10Ni | 2.8 |
| 30Ni10Ce | 3.1 |
| 30Ni10La | 3.9 |

A decrease in carbon deposition amounts was observed in the order of 30Ni10La>30Ni10Ce>30Ni10Ni>30Ni10Co>30Ni10Fe catalysts.

Example 1: Methanation Reaction of Carbon Monoxide Using Nickel-M-Alumina Xerogel Catalyst A methanation reaction on a synthetic gas including carbon monoxide and hydrogen was performed using the nickel-M-alumina xerogel catalysts prepared in Preparation Examples 1 and 2 to prepare methane.

Before the reaction, the prepared catalysts were reduced for 5 hours while allowing nitrogen (30 ml/min) and hydrogen (3 ml/min) to flow simultaneously at 700° C. in a continuous flow reactor for a methanation reaction.

The continuous flow reactor was a stainless steel reactor which was installed in an electric oven so as to maintain a constant reaction temperature by means of a temperature regulator. Then, a reaction was performed while continuously passing reaction products through a catalyst layer in the continuous flow reactor. Amounts of carbon monoxide, hydrogen and nitrogen used in this reaction were adjusted using a mass flow rate regulator, and the reaction was performed under a predetermined pressure using a pressure regulator.

Figure 5:
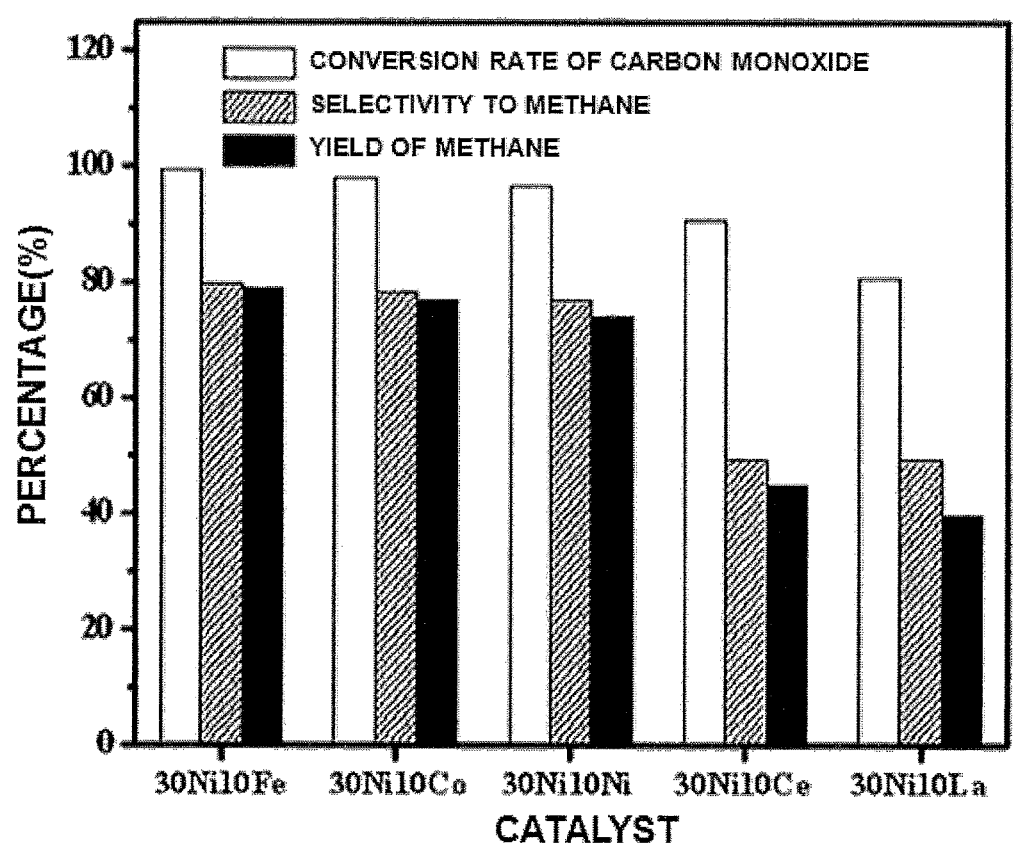
FIG. 5 is a graph illustrating the carbon monoxide conversion rate, methane selectivity and methane yield during a hydrogenation reaction of carbon monoxide using the nickel-M-alumina xerogel catalysts prepared in Preparation Examples 1 and 2.

The compositions of the reaction product were adjusted so that nitrogen, carbon monoxide and hydrogen were present at a volume ratio of 1.67:1:3, and the space velocity was set to 8,160 ml/h·g-catalyst. The reaction temperature was maintained at 230° C., and the reaction pressure was maintained at 10 bars. Also, the reactor used in the reaction is shown in FIG. 5.

The products after a hydration reaction of carbon monoxide by each of the nickel-M-alumina xerogel catalysts prepared in Preparation Examples 1 and 2 were analyzed using gas chromatography, and the conversion rate of carbon monoxide, conversion rate of hydrogen, hydrocarbon selectivity, carbon dioxide selectivity and methane yield were calculated. The results are listed in Table 3 and shown in FIG. 6 (after 600 minutes from a reaction time).

The conversion rates of carbon monoxide and hydrogen and the selectivity of hydrocarbon and carbon dioxide by the nickel-M-alumina xerogel catalyst were calculated using the following Equations 1 to 4. The methane yield was calculated by multiplying the conversion rate of carbon monoxide by the methane selectivity.

$$\text{Conversion rate of carbon monoxide (\%)} = \frac{\text{Mole of reacted carbon monoxide}}{\text{Mole of supplied carbon monoxide}} \times 100 \quad \text{Equation 1}$$

$$\text{Conversion rate of hydrogen (\%)} = \frac{\text{Mole of reacted hydrogen}}{\text{Mole of supplied hydrogen}} \times 100 \quad \text{Equation 2}$$

$$\text{Selectivity of hydrocarbon } (C_n+) \text{ (\%)} = \frac{\text{Mole of hydrocarbon } (C_n+) \text{ in products}}{\text{Sum of moles of all products excluding water}} \times 100 \quad \text{Equation 3}$$

$$\text{Selectivity of carbon dioxide (\%)} = \frac{\text{Mole of carbon dioxide in products}}{\text{Sum of moles of all products excluding water}} \times 100 \quad \text{Equation 4}$$

be deposited on a surface of the catalyst as a stable carbon species having no reactivity. The temperature-programmed surface reaction results of carbon monoxide adsorbed at room temperature showed carbon monoxide dissociation energies of the respective catalysts, which indicates that carbon (C) in an intermediate form appeared on a surface of the catalyst since carbon monoxide was more easily dissociated by the catalyst by which a peak of methane appears at a low temperature, compared with the other catalysts. From the temperature-programmed surface reaction results, it was revealed that a decrease in temperature at which methane was produced was set in the order of 30Ni10Fe, 30Ni10Ni, 30Ni10Co, 30Ni10Ce and 30Ni10La.

It could be seen that this order was slightly different from the reaction results of methanation reaction by the catalyst. To compare the methanation reaction results with the temperature-programmed surface reaction results, the relationship between the methane generation temperatures and the methane yields in the temperature-programmed surface reaction by the respective catalysts is shown in FIG. 5. From the temperature-programmed surface reaction results by the 30Ni10Ni catalyst, it could be seen that the methane generation temperature was set to a level lower than that of the 30Ni10Co catalyst. From the methanation reaction results, however, it could be seen that the methane yield was approximately 2.8% lower than that of the 30Ni10Co catalyst. This difference could be explained by the carbon deposition amounts listed in Table 2. The adsorbed carbon monoxide was dissociated into intermediate carbon and oxygen at a temperature corresponding to a specific dissociation energy of each catalyst. The intermediate carbon could bind to hydrogen to form methane, and also take part in a methanation reaction as a stable carbon species on a surface of the catalyst. Carbon (C) was deposited at a decreasing amount in the order of the 30Ni10Fe, 30Ni10Co, 30Ni10Ni, 30Ni10Ce and 30Ni10La catalysts. From the methanation reaction results, the temperature-programmed surface reaction and carbon deposition results showed that, in the case of the 30Ni10Ni catalyst, a dissociation energy of carbon monoxide was lower than that of the 30Ni10Co catalyst, but a level of intermediate carbon converted into a stable carbon species was higher than that of the 30Ni10Co

TABLE 3

| Catalyst | Conversion rate | | Compositions of hydrocarbon in product (mole %) | | | | | Carbon dioxide in carbon product (mole %) | Methane yield |
| --- | --- | --- | --- | --- | --- | --- | --- | --- | --- |
| | CO | $H_2$ | $C_1$ | $C_2$ | $C_3$ | $C_4$ | $C_5+$ | | |
| 30Ni10Fe | 99.4 | 86.8 | 79.6 | 6.5 | 2.4 | 1.1 | 0.6 | 9.8 | 79.1 |
| 30Ni10Co | 98.0 | 87.7 | 78.4 | 7.1 | 3.3 | 1.7 | 1.1 | 8.4 | 76.8 |
| 30Ni10Ni | 96.5 | 88.0 | 76.8 | 8.1 | 4.8 | 2.8 | 1.9 | 5.6 | 74.1 |
| 30Ni10Ce | 90.7 | 72.3 | 49.5 | 8.6 | 11.3 | 9.5 | 10.8 | 10.3 | 44.9 |
| 30Ni10La | 80.8 | 67.1 | 49.2 | 8.3 | 12.1 | 10.3 | 13.3 | 6.8 | 39.8 |

Figure 6:
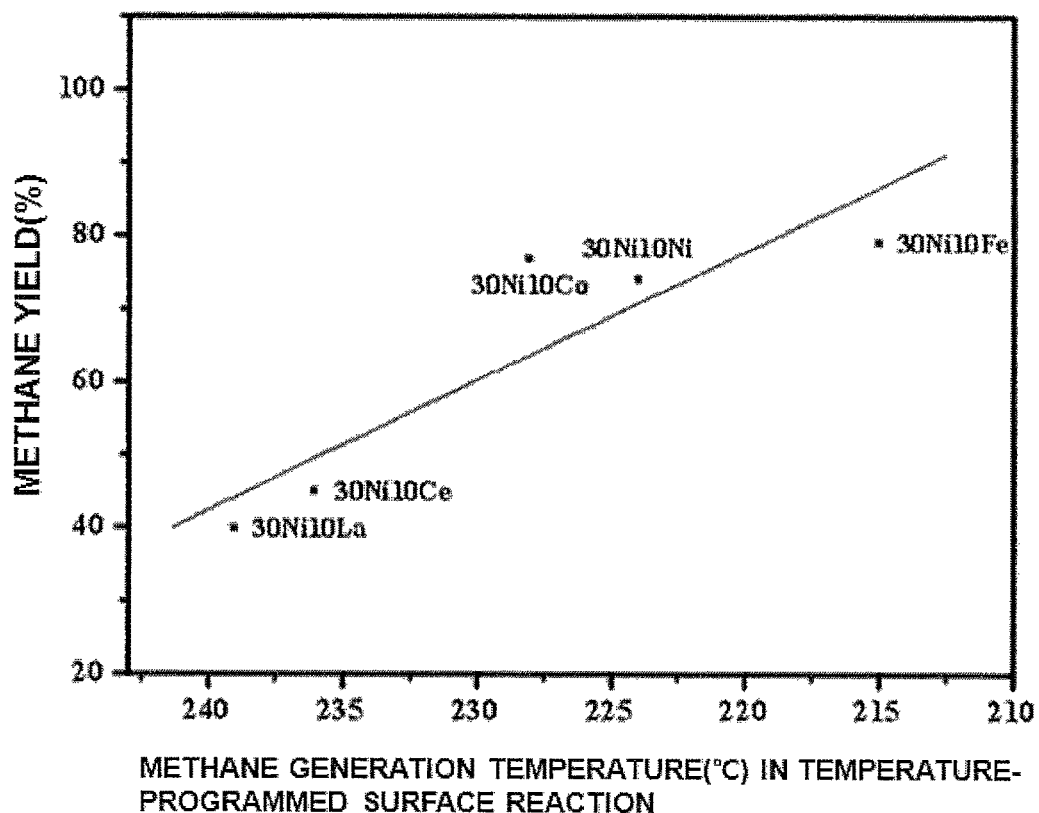
FIG. 6 is a graph illustrating the temperature-programmed surface reaction results of the nickel-M-alumina xerogel catalysts prepared in Preparation Examples 1 and 2, and the correlation with a methane yield.

As listed in Table 3 and shown in FIG. 6, it could be seen that the conversion rate of CO, CO selectivity, and methane yield were shown to be high in the order of the 30Ni10Fe>30Ni10Co>30Ni10Ni>30Ni10Ce>30Ni10La catalysts. These results could be derived from the temperature-programmed surface reaction results and a deposition amount of carbon (C) by the catalyst after a methanation reaction. An important operation of determining reactivity in a hydrogenation reaction of carbon monoxide is dissociation of carbon monoxide. The dissociated intermediate carbon may bind to hydrogen to be converted into methane, or may catalyst. Accordingly, the methanation reaction results showed that a yield of methane was 2.8% lower than that of the 30Ni10Co catalyst. In the case of the 30Ni10Fe catalyst, a dissociation energy of carbon monoxide was lower than those of the other catalysts, and a carbon deposition amount was also lower than those of the other catalysts. This indicates that the intermediate carbon produced on the 30Ni10Fe catalyst is converted into methane at a high ratio. From all these results, it could be seen that, among the catalysts, the 30Ni10Fe catalyst had the highest activity to perform a methanation reaction.

From the temperature-programmed surface reaction results, it could be seen that the methane generation temperature was set to a level lower than that of the 30Ni10Co catalyst. From the methanation reaction results, however, it could be seen that the methane yield was approximately 2.8% lower than that of the 30Ni10Co catalyst. This difference could be explained by the carbon deposition amounts listed in Table 2. The adsorbed carbon monoxide was dissociated into intermediate carbon and oxygen at a temperature corresponding to a specific dissociation energy of each catalyst. The intermediate carbon could bind to hydrogen to form methane, and also take part in a methanation reaction as a stable carbon species on a surface of the catalyst. Carbon (C) was deposited at a decreasing amount in the order of the 30Ni10Fe, 30Ni10Co, 30Ni10Ni, 30Ni10Ce and 30Ni10La catalysts. From the methanation reaction results, the temperature-programmed surface reaction and carbon deposition results showed that, in the case of the 30Ni10Ni catalyst, a dissociation energy of carbon monoxide was lower than that of the 30Ni10Co catalyst, but a level of intermediate carbon converted into a stable carbon species was higher than that of the 30Ni10Co catalyst. Accordingly, the methanation reaction results showed that a yield of methane was 2.8% lower than that of the 30Ni10Co catalyst. In the case of the 30Ni10Fe catalyst, a dissociation energy of carbon monoxide was lower than those of the other catalysts, and a carbon deposition amount was also lower than those of the other catalysts. This indicates that the intermediate carbon produced on the 30Ni10Fe catalyst is converted into methane at a high ratio. From all these results, it could be seen that, among the catalysts, the 30Ni10Fe catalyst had the highest activity to perform a methanation reaction.

The catalyst according to one exemplary embodiment of the present invention has strong resistance against a high-temperature sintering reaction and deposition of carbon species, and can effectively improve a conversion ratio of carbon monoxide and selectivity to methane.

The catalyst according to one exemplary embodiment of the present invention can be widely used in the field of methane synthesis.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A nickel-M-alumina hybrid xerogel catalyst for preparing methane comprising, a nickel-M-alumina hybrid xerogel catalyst wherein the metal M is Co,
    wherein, the nickel-M-alumina hybrid xerogel catalyst includes nickel at 15 to 45 parts by weight, and Co at 5 to 15 parts by weight, based on a total of 100 parts by weight of the catalyst,
    wherein the catalyst prepares methane through a hydrogenation reaction of carbon monoxide,
    wherein pores formed in the catalyst have an average diameter of 2 to 4 nm, and
    wherein a conversion rate of carbon monoxide is in a range of 98 to 99.4% and selectivity to methane in a hydrocarbon is in a range of 60 to 90% during a hydrogenation reaction, when a reaction temperature is maintained at 230° C. and a reaction pressure is maintained at 10 bars.

2. The nickel-M-alumina hybrid xerogel catalyst of claim 1, wherein the catalyst has a specific surface area of 100 to 350 m$^2$/g.

* * * * *